United States Patent [19]

Sleezer et al.

[11] 4,185,015
[45] Jan. 22, 1980

[54] METHOXYMETHYL 6-[D-2,2-DIMETHYL-4-(4-HYDROXYPHENYL)-5-OXO-1-IMIDAZOLYL]PENICILLANATE

[75] Inventors: Paul D. Sleezer, Dewitt; David A. Johnson, Fayetteville, both of N.Y.

[73] Assignee: Bristol-Myers Company, New York, N.Y.

[21] Appl. No.: 838,618

[22] Filed: Oct. 3, 1977

Related U.S. Application Data

[63] Continuation-in-part of Ser. No. 744,572, Nov. 24, 1976, abandoned, which is a continuation of Ser. No. 549,109, Feb. 11, 1975, abandoned, which is a continuation-in-part of Ser. No. 341,196, Mar. 24, 1973, abandoned.

[51] Int. Cl.$^2$ .......................................... C07D 499/80
[52] U.S. Cl. .................. 260/239.1; 424/271; 260/245.2
[58] Field of Search .................. 260/239.1, 306.7 C

[56] References Cited

U.S. PATENT DOCUMENTS

| 3,652,546 | 3/1972 | Cheney et al. | 260/239.1 |
| 3,864,332 | 2/1975 | Rabinovich et al. | 260/239.1 |

FOREIGN PATENT DOCUMENTS

| 1217143 | 12/1970 | United Kingdom | 260/239.1 |
| 1224619 | 3/1971 | United Kingdom | 260/239.1 |

OTHER PUBLICATIONS

Jansen et al., J. Chem. Soc., pp. 2127–2132, (1965).
Jackson et al., Chem. Comm., pp. 14–15, (1970).

*Primary Examiner*—Gerald A. Schwartz
*Attorney, Agent, or Firm*—Herbert W. Taylor, Jr.

[57] ABSTRACT

There is disclosed a process for preparing methoxymethyl 6-aminopenicillanate, its conversion to methoxymethyl amoxicillin and the use of the latter compound as an intermediate in the preparation of the methoxymethyl ester of p-hydroxyhetacillin which is the preferred product of this invention.

2 Claims, No Drawings

METHOXYMETHYL 6-[D-2,2-DIMETHYL-4-(4-HYDROXYPHENYL)-5-OXO-1-IMIDAZOLYL]PENICILLANATE

CROSS-REFERENCE TO RELATED APPLICATIONS

This application is a continuation-in-part of our prior, copending U.S. application Ser. No. 744,572 filed Nov. 24, 1976 and now abandoned which was in turn a continuation of our prior, copending U.S. application Ser. No. 549,109 filed Feb. 11, 1975 and now abandoned which was in turn a continuation-in-part of our prior, copending application Ser. No. 341,196 filed Mar. 24, 1973 and now abandoned. In addition, another continuation-in-part of Ser. No. 341,196 was filed Feb. 18, 1975 as Ser. No. 550,317 and issued Dec. 7, 1976 as U.S. Pat. No. 3,996,236.

BACKGROUND OF THE INVENTION (1) Field of the Invention

The antibiotic compound of this invention is a derivative of p-hydroxy-hetacillin and amoxicillin.

(2) Description of the Prior Art

Hetacillin is a penicillin derivative known, in the acid form, as D-6-(2,2-dimethyl-5-oxo-4-phenyl-1-imidazolidinyl)penicillanic acid. This compound, i.e., hetacillin, and many closely related compounds and the preparation thereof are disclosed in U.S. Pat. No. 3,198,804. Esters of benzylpenicillins are disclosed in British Pat. No. 1,003,479 and U.S. Pat. No. 2,650,218, and acyloxymethyl esters of ampicillin are discussed by W. v. Daehne et al. in *J. Med. Chem.*, 13, (4), 607–612 (1970). This publication also refers to early publications on the hydrolysis of esters. The pivaloyloxymethyl ester of ampicillin is also disclosed in U.S. Pat. Nos. 3,660,575 and 3,697,507. Various penicillin esters are also disclosed, for example, in U.S. Pat. No. 3,528,965 and U.K. No. 1,267,936. Various esters of 6-aminopenicillanic acid have been disclosed, for example, in U.S. Pat. Nos. 3,652,546 and 3,399,207. The crystalline toluene-p-sulphonate of the methoxymethyl ester of 6-aminopenicillanic acid was described by Jackson et al., *Chemical Communications*, 1970, pages 14–15. Methoxymethyl benzylpenicillinate and other penicillin esters are described by Jansen et al., *J. Chem. Soc.*, 2127–32 (1965) and that publication refers to earlier publications such as Johnson, *J. Amer. Chem. Soc.*, 75, 3636 (1953) and Barnden et al., *J. Chem. Soc.*, 3733 (1953). The Jansen et al. publication is referred to in U.K. No. 1,217,143 published Dec. 31, 1970 (but not in the corresponding U.S. Pat. No. 2,650,218) in its generic disclosure on page 2 which names various specific esters of penicillins, including methoxymethyl, and suggests acylation of those and other esters of 6-aminopenicillanic acid (6-APA) with "any of the acyl groups found in the side chains of known antibacterial penicillins, especially the group of" the formula for D-(−)-2-phenylglycine which occurs in ampicillin.

Amoxicillin [also known as D-6-(p-hydroxy-α-aminophenylacetamido)penicillanic acid] is disclosed in U.S. Pat. Nos. 3,192,198 and 3,674,776; p-hydroxyhetacillin is disclosed in U.K. No. 1,224,619.

Subsequent to the filing on Sept. 13, 1971 of the parent of this application in the United States there appeared abroad applications corresponding to said parent application U.S. Ser. No. 180,070 as exemplified by U.S. Pat. No. 3,996,236 and by Belgium No. 788,720 to Bristol-Myers Company reported and abstracted as Farmdoc 18226U by Derwent Publications Ltd, Rochdale House, 128 Theobalds Road, London WC1X 8RP, England, in the issue of Central Patents Index—Basic Abstracts Journal—B—Farmdoc dated May 17, 1973. In the issue of Feb. 8, 1973 Belgium No. 784,800 to Yamanouchi Pharmaceutical Co., Ltd. was abstracted as Farmdoc 81300T; this Belgian patent generically claims, inter alia, compounds of the formula

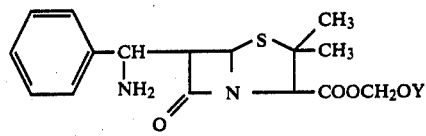

wherein Y is, inter alia, lower alkyl and also contains working examples wherein Y is ethyl and some higher homologs and contains on page 4 a reference to the use of chloromethyl methyl ether (Y equals methyl).

SUMMARY OF THE INVENTION

This invention is thus directed to the preparation of the acetone adduct of methoxymethyl ester of amoxicillin. The term acetone adduct refers to the product obtained by reacting the appropriate α-amino compound with a stochiometric amount of acetone to obtain a product described by structure I below.

This compound is described by the structure:

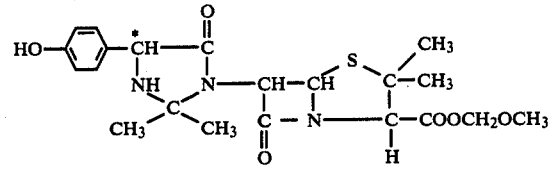

having the D- configuration at the carbon atom marked with an asterisk. It may be named methoxymethyl D-6-[2,2-dimethyl-5-oxo-4-(p-hydroxyphenyl)-1-imidazolidinyl]-penicillanate. For convenience, this compound can be referred to as p-hydroxy-hetacillin methoxymethyl ester.

There is also provided by the present invention the process for preparing the methoxymethyl ester of p-hydroxyhetacillin which comprises the consecutive steps of (a) forming a penicillin ester of the formula

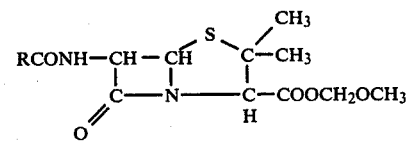

wherein R is an organic radical, (b) deacylating said penicillin ester to form methoxymethyl 6-aminopenicillanate, (c) reacylating said methoxymethyl 6-amino-penicillanate with the acyl moiety of D-(−)-2-p-hydroxyphenylglycine to produce the methoxymethyl ester of amoxicillin, and (d) reacting said methoxymethyl ester of amoxicillin with acetone to produce the methoxymethyl ester of p-hydroxyhetacillin wherein preferably R is phenoxymethyl and preferably step d is conducted at a pH in the range of 5.5 to 9.5 and better yet step d is conducted at a pH in the range of 7.5 to 9.5.

In general, the methoxymethyl ester of hetacillin or of amoxicillin can be prepared by reacting with a suitable esterifying derivative of dimethyl ether, such as a halomethyl methyl ether, a fermentation-produced penicillin, such as phenoxymethyl penicillin, after which the phenoxymethyl penicillin ester so produced is deacylated by known procedures to provide the corresponding methoxymethyl ester of 6-aminopenicillanic acid. This 6-APA ester and a suitable acylating agent can then be reacted as shown herein.

The 6-APA ester can be acylated by known procedures to provide various penicillin esters according to the choice of acylating agents. The choice of acylating agent and conditions for acylation are not narrowly critical. Either the free acid, that is, D-(−)-2-p-hydroxyphenylglycine, or its equivalent can be employed to acylate the free amino group of the 6-APA ester. Such acylating agents include the free acid and the corresponding carboxylic acid halides, e.g., the chlorides and bromides; the acid anhydrides, including mixed anhydrides and particularly the mixed anhydrides prepared from acids such as the lower aliphatic monoesters of carbonic acid, of alkyl and aryl sulfonic acid and of more hindered acids, such as diphenylacetic acid. In addition, an acid azide or an active ester of thioester (e.g., with p-nitrophenol, 2,4-dinitrophenol, thiophenol, thioacetic acid) may be used or the free acid itself may be coupled with 6-aminopenicillanic ester after first reacting said free acid with N,N'-dimethylchloroformiminium chloride [cf. Great Britain No. 1,008,170 and Novak and Weichet, Experientia XXI/6, 360 (1965)] or by the use of enzymes or of an N,N'-carbonyldiimidazole or an N,N'-carbonylditriazole [cf. South African Patent Specification No. 63/2684] or of a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1067 (1955)], or of alkynylamine reagent [cf. R. Buijle and H. G. Viehe, Angew. Chem. International Edition, 3, 582 (1964)], or of a ketenimine reagent [cf. C. L. Stevens and M. E. Monk, J. Amer. Chem. Soc., 80, 4065 (1958)] or of an isoxazolium salt reagent [cf. R. B. Woodward, R. A. Olofson and H. Mayer, J. Amer. Chem. Soc., 83, 1010 (1961)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)] and it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer. Chem. Soc., 90, 823–824 and 1652–1653 (1968).

Another equivalent of the acid is a corresponding azolide, i.e., an amide of the acid the amide nitrogen of which is a member of a quasi-aromatic five-membered ring containing at least two nitrogen atoms, i.e., imidazole, pyrazole, the triazoles, benzimidazole, benzotriazole, and their substituted derivatives. As an example of the general method for the preparation of an azolide, N,N'-carbonyldiimidazole is reacted with a carboxylic acid in equimolar proportions at room temperature in tetrahydrofuran, chloroform, dimethyl-formamide or a similar inert solvent to form the carboxylic acid imidazolide in practically quantitative yield with liberation of carbon dioxide and one mole of imidazole. Dicarboxylic acids yield diimidazolides. The by-product, imidazole, precipitates and may be separated and the imidazolide isolated, but this is not essential. The methods for carrying out these reactions to produce a penicillin and the methods used to isolate the penicillin so produced are well known in the art (cf. U.S. Pat. Nos. 3,079,314, 3,117,126, 3,129,224 and British Pat. Nos. 932,644, 957,570 and 959,054).

Mention was made above of the use of enzymes to couple the free acid with methoxymethyl 6-aminopenicillanate. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

In a case such as this where the acylating agent contains a free amino group, it may be desirable to protect it with a suitable blocking agent. Such protecting groups include those of the general formula ROCO—in which R is an allyl, benzyl, substituted benzyl, phenyl, substituted phenyl, or trityl group. It is usually preferred, however, to use D-(−)-2-p-hydroxyphenylglycyl chloride hydrochloride as the acylating agent.

Another preferred process consists of (a) acylating the methoxymethyl ester of 6-aminopenicillanic acid with an acid in the D- configuration of the formula

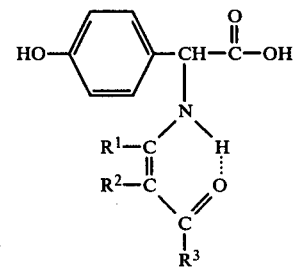

wherein $R^1$ is alkyl, aralkyl or aryl, $R^2$ is hydrogen, alkyl, aralkyl or aryl and $R^3$ is alkyl, aralkyl, aryl, alkoxy, aralkoxy, aryloxy or

wherein $R^4$ and $R^5$ are each hydrogen, alkyl, aralkyl or aryl or, when taken together with the nitrogen atom, are piperidino or morpholino, or an acylating derivative thereof in an inert solvent at a temperature below 0° C., and (b) removing the α-amino-protecting group.

In this process it is preferred that there is also present during step (a) a compound of the formula

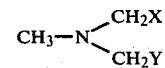

wherein X is a hydrogen atom or an alkyl or phenyl group, Y is a hydrogen atom or a lower alkyl group, or X and Y together represent any one of the divalent radicals, ethylene, substituted ethylene, trimethylene, —CH$_2$OCH$_2$— or —CH$_2$N(CH$_3$)CH$_2$—. Examples of such catalysts are N-methylmorpholine and N,N-dimethylbenzylamine. It is preferred that the inert solvent be acetone or aqueous acetone or tetrahydrofuran and that the acylating derivative be a mixed anhydride formed from an alkyl chlorocarbonate.

It is further preferred that, in the en-amine amino-protecting group, R$^1$ is methyl, R$^2$ is hydrogen and R$^3$ is methoxy, ethoxy or methyl; this requires the use of methyl acetoacetate, ethyl acetoacetate or acetylacetone.

In the removal of the α-amino-protecting group it is preferred that use be made of a strong mineral acid such as hydrochloric acid or of formic acid.

The resulting penicillin ester, e.g., the methoxymethyl ester of amoxicillin, is then reacted with acetone to form the acetone adduct ester, e.g., p-hydroxyhetacillin ester, in accordance with the procedure disclosed in the U.S. Pat. No. 3,198,804. Thus in performing this reaction the proportions of each reactant are not critical and some reaction will occur regardless of the proportions of reactants. It is preferred, however, to use at least a one mole excess of acetone in order to obtain maximum yields. Larger molar excesses of acetone may be used and indeed the acetone may comprise the reaction medium as well as being a reactant. The reaction medium may be anhydrous or aqueous. The reaction is an equilibrium reaction during which water is split off and it is therefore preferred not to have a major amount of water present in the reaction medium.

The pH of the reaction mixture during the formation of this p-hydroxyhetacillin ester should be from about 5.5 to about 9.5 and is preferably from about 7.5 to 9.5. The pH may be adjusted to within this range, if necessary, by the addition of an alkaline material, for example, sodium hydroxide, sodium carbonate, potassium hydroxide, potassium carbonate, ammonium hydroxide, ammonium carbonate or organic amines, e.g., triethylamine.

The temperature during the reaction is not critical. The reaction will proceed satisfactorily at room temperature and may be hastened by heating.

Broadly, this process involves esterification of a natural penicillin of the structure

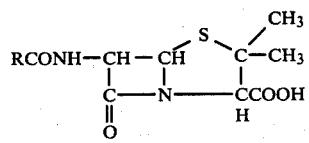

wherein R is an organic radical of which many are well known in the penicillin art. The acyl group of any of the well known natural penicillins can be employed. A particularly suitable side chain is the phenoxymethyl group.

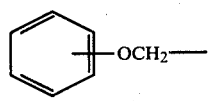

Illustrative organic radicals include benzyl, furylmethyl, thienylmethyl and the like. As is well known, the various organic radicals can be substituted.

More particularly, in the process of this invention a salt of phenoxymethyl penicillin in a suitable reaction medium is reacted with chloromethyl methyl ether or bromomethyl methyl ether at a temperature between about 0° C. and 50° C. and preferably between 0° C. and about 30° C. A preferred reaction medium is methylene chloride to which may be added some dimethylformamide generally in a ratio of about 1 to 2 ml. per 150 ml. of methylene chloride. Dimethylformamide can also be used as a reaction medium. The reaction product can be recovered by conventional methods.

The recovered ester of phenoxymethyl penicillin is then deacylated, either enzymatically or chemically. Enzymatic production of 6-APA by deacylation of a penicillin is disclosed in U.S. Pat. No. 3,014,846. The preferred method of chemical cleavage is carried out by forming an imino halide by reaction with a halogenating agent, such as phosphorous pentachloride. The ester is dissolved in a non-aqueous solvent, such as methylene chloride, benzene or chloroform, to which there has been added a suitable amount of an acid-binding agent, such as dimethylaniline, pyridine, quinoline, or lutidine. The amount of acid-binding agent should be sufficient to take up the acid formed by the cleavage reaction. The chlorination reaction temperature should be maintained between about −50° C. to about 0° C. to provide complete chlorination of the ester. The imino chloride is then treated with an alcohol under acid conditions whereby an imino ether is formed under anhydrous conditions. Water is then added to the reaction mixture to hydrolyze the ether. The imino ether can conveniently be formed at temperatures of from about −70° C. to about −30° C.

The general procedure for this series of reactions is disclosed in U.S. Pat. No. 3,499,909, along with various halogenating agents, acid-binding agents, alcohols, and solvents all of which are generally applicable to the herein disclosed methoxymethyl esters. Thus, the 6-APA ester can be isolated from the reaction mixture as the free base or as an acid addition salt such as the p-toluene-sulfonate salt.

Acylation of the 6-APA ester to provide the methoxymethyl ester of amoxicillin can be achieved following known procedures, such as those disclosed in U.S. Pat. Nos. 2,985,648 and 3,140,282.

The above-mentioned p-toluenesulfonate salt of the methoxymethyl ester of 6-APA is then contacted with an acylating agent, such as D-(−)-2-p-hydroxyphenylglycyl chloride hydrochloride, in either anhydrous methylene chloride or in an acidic aqueous medium at low temperature. Broadly, the acylating agent is employed in amounts of about 1 to 3 moles per mole of 6-APA, and the temperature should be between about −10° C. and +20° C. The pH of the reaction medium should be below 4 and preferably from about 1.5 to about 3.0, usually between 2.0 and 2.8. The reaction medium is often a mixture of water and organic solvents such as acetone, methylene chloride, or tetrahydrofuran. The acylated ester is recovered by raising the pH of the reaction medium to about 4 or above, e.g., between 4 and 7. Any solids are removed by filtration to provide a solution of the amoxicillin ester.

In a preferred procedure, the ester is dissolved in methylene chloride-acetone mixture at ice bath temperatures generally between about 0° C. and 5° C. A small amount of water, about 2.5% based on the volume of the organic solvent, is then added, preferably in about stochiometric amounts. The resulting admixture is maintained at about 0° C. until the acid chloride has dissolved. The reaction product can then be recovered by standard methods. This reaction can be run under anhydrous conditions.

The amoxicillin methoxymethyl ester is then converted to the corresponding p-hydroxy-hetacillin ester by reaction with aqueous acetone at a pH of from about 6.5 to about 9.5. In general, this step of the process is carried out at a temperature between about −10° C. and 15° C., although it is generally preferred to employ temperatures of about 0° C. to about 5° C. The pH and temperature should be maintained for a period of time which is sufficient to provide substantial conversion to p-hydroxy-hetacillin, e.g., from about 12 to 170 hours, depending on the other conditions. After the reaction period, the p-hydroxy-hetacillin methoxymethyl ester is recovered by adjusting the pH of the reaction mixture to between 1.5 and 2.0 with an acid such as hydrochloric acid and extracting with a suitable solvent such as methylene chloride. The p-hydroxy-hetacillin ester is recovered from the organic phase in the usual manner.

A useful embodiment of the process of this invention is a continuous series of reactions carried out without isolation or recovery of intermediates. For example, the potassium salt of phenoxymethyl penicillin is esterified with bromo- or chloro-methyl methyl ether in methylene chloride at a temperature between 0° C. and 30° C. The methylene chloride solution of the ester is then successively treated with phosphorus pentachloride, methyl alcohol, and water to complete removal of the phenoxymethyl side chain and provide a methylene chloride solution containing the methoxymethyl ester of 6-APA. This solution is then carried forward and used in the acylation reaction in which D-(−)-2-p-hydroxyphenylglycyl chloride hydrochloride is added to the solution to give a methylene chloride solution of the amoxicillin ester. In the final step, the solution of amoxicillin ester is treated with acetone at pH 7.5 to 8.5 and held until p-hydroxy-hetacillin ester formation has proceeded.

The following examples are given in illustration of, but not in limitation of, the present invention. All temperatures are in degrees Centigrade. Methyl isobutyl ketone is represented as MIBK.

DESCRIPTION OF THE PREFERRED EMBODIMENTS

EXAMPLE 1

Methoxymethyl Ester of Penicillin V.

Potassium phenoxymethylpenicillinate (38.8 grams) was slurried in 150 ml. of methylene chloride and the mixture cooled to about 5° C. by means of a cooling bath, and 9.5 grams (0.118 mole) of chloromethyl methyl ether and 0.5 ml. of dimethylformamide was added. The cooling bath was removed and the mixture stirred for about 1.5 hours while allowing the mixture to come to room temperature. The methylene chloride solution was washed four times with 200 ml. portions of water and then dried and stripped of solvent by distillation in vacuo to give 33.5 grams of methoxymethyl ester of penicillin V as a yellowish oil. The yield was about 84%.

EXAMPLE 2

Preparation of Pen V Methoxymethyl Ester

To 100 g. (0.257 mole) of K Pen V (potassium phenoxymethylpenicillin) slurried in 300 ml. of dry dichloromethane and cooled to 0°–5° C. was added over about 10 min., 32.12 g. (0.257 mole) of bromomethyl methyl ether in 60 ml. dichloromethane. After the addition, 1 ml. of DMF (dimethylformamide) was added and the reaction was allowed to proceed 3 hr. at 0°–5° C. Tlc (thin layer chromatography) (50/50 acetone/benzene) showed a major zone for product, Rf about 0.7.

The reaction mixtue was washed with 3×100 ml. portions of water, dried over MgSO₄ and concentrated under reduced pressure at about 40° to an oil. The oil was taken up in 300 ml. of 2-propanol at about 25°, seeded and crystallized 12 hr. at 0°–5°. The white crystals were collected by filtration and washed with 2-propanol, followed by heptane, and gave after drying at about 25° in a vacuum oven for about 4 hr. 68 g. (about 67% yield) of Pen V methoxymethyl ester homogeneous on tlc and showing consistent and clean ir and nmr spectra.

EXAMPLE 3

6-APA Methoxymethyl Ester as its p-Toluenesulfonate.

To 57 g. (0.145 mole) of Pen V methoxymethyl ester dissolved in 500 ml. CH₂Cl₂ and cooled to −30° C. was added 37 ml. of N,N-dimethylaniline, followed by 33.1 g. of phosphorous pentachloride. The mixture was stirred at −30° C. for 90 min. Tlc showed almost no residual methoxymethyl ester of Pen V. The mixture was cooled to about −60° C. and 150 ml. of precooled (−50° C.) methanol was added in one portion. The temperature was then held at about −40° C. for 2 hours. The solution was then added rapidly to 150 ml. of 0°–5° water and held for 10 min. at 0° to 5° C. The pH was about 0.8.

Maintaining this temperature range, 10% NaOH solution was used to adjust to pH 6.9. The layers were separated and the dichloromethane layer washed with 3×100 ml. portions of cold water. After drying over magnesium sulfate, the CH₂Cl₂ layer was concentrated under vacuum to about half volume and 54 g. (0.284 mole) of p-toluenesulfonic acid dissolved in 120 ml. of acetone was added. Seed crystals of product were added and the mixture crystallized at 0° to 5° C. for 2 hr. After collecting by filtration, washing with 100 ml. of 50/50 CH₂Cl₂/heptane and drying in a circulating air oven at about 30° C. for 4–6 hr., there was obtained 23.7 g. (37.8% yield) of the p-toluenesulfonic acid salt of 6-APA methoxymethyl ester.

EXAMPLE 4

6-aminopenicillanic Acid Methoxymethyl Ester.

To a solution of 12 grams (0.0304 mole) of penicillin V methoxymethyl ester in 100 ml. of methylene chloride cooled to −55° C., there was added 4.8 ml. (4.6 grams, 0.038 mole) of dimethylaniline and this followed directly by 7.0 grams (0.0337 mole) of phosphorous pentachloride dissolved in 100 ml. of methylene chloride.

The mixture was held at −40° C. to −50° C. for about 2 hours. Thin layer chromatography indicated complete chlorination of the pen V ester. The mixture was then cooled to −70° C. and 47 ml. of methanol, precooled to −50° C., was added rapidly. The mixture was then held for 2 hours at −50° C. to −40° C. To the resulting yellow solution, 100 ml. of water was added with vigorous agitation. The temperature of the reaction mixture rose to about 0° C., and the pH of the mixture was about 0.6 to 1.0. After holding the mixture for about 10 to 15 minutes at this temperature and pH range, the pH was brought to 6.5 to 6.8 with dilute sodium hydroxide. The layers were separated and the methylene chloride layer was washed with water, carbon treated, and dried to yield the desired methoxymethyl 6-amino-penicillinate. Thin layer chromatography showed that this solution contained dimethyl aniline, methyl phenoxyacetate, and 6-APA methoxymethyl ester.

EXAMPLE 5

Amoxicillin Methoxymethyl Ester.

To 30 ml. of dry CH$_2$Cl$_2$ at 0° to 5° C. was added 2.16 g. (0.005 mole) of the p-toluenesulfonic acid salt of methoxymethyl 6-aminopenicillanate followed by 0.7 ml. (0.005 mole) of triethylamine. To the resulting clear solution was added 0.64 ml. (0.005 mole) of dimethylaniline, followed by 1.33 g. (0.005 mole) of D-(−)-p-hydroxyphenylglycyl chloride hydrochloride hemidioxane solvate added in about 5 min. After about 1 to 1.5 hr. when nearly all the solid acid chloride had dissolved, the reaction mixture was quenched into 30 ml. of cold water. The pH was brought to 3.0 using sodium bicarbonate solution and the layers separated. Maintaining pH 3.0 and 0° to 5° C. the water layer was further washed with 4×30 ml. of CH$_2$Cl$_2$. This removes most of the dimethylaniline and leaves the product in the H$_2$O. Using NaHCO$_3$ the water layer was then adjusted to pH 7.5 and extracted 2×30 ml. CH$_2$Cl$_2$. The combined CH$_2$Cl$_2$ layers were washed with 2×20 ml. H$_2$O, dried over MgSO$_4$ and concentrated under reduced pressure at <40° to give amoxicillin methoxymethyl ester as a friable, foamy solid weighing 1.82 g. (about 88% yield) homogeneous on tlc and having infrared and 100 MHz nmr spectra consistant for the methoxymethyl ester of amoxicillin.

NMR: CD$_2$Cl+CD$_3$OD solvent

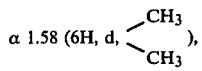

3.5 (3H,s,OCH$_3$), 4.5 (2H, overlapping singlets, C-3 and phenyl glycyl H), 5.35 ("3H" AB quartet, O—CH$_2$—O plus some CH$_2$Cl$_2$ in solvent), 5.6 (2H, AB quartet, β-lactam H$_2$), 6.9 (4H, AB quartet, aromatic H).

A 20 mg. sample of the ester was dissolved in 10 ml. of 50/50 acetone/pH 7.0 buffer and showed a bioassay of 1968 mcg./ml. of amoxicillin (about 110% of theory).

EXAMPLE 6 p-Hydroxy-Hetacillin Methoxymethyl Ester Hydrochloride.

A 10 g. sample of methoxymethyl p-hydroxyhetacillin was dissolved in 80 ml. of dry acetone and 6 ml. of 13% hydrogen chloride in 2-propanol was added. The solution was then poured rapidly into 1,000 ml. of well stirred diethyl ether. After 5 minutes of vigorous agitation, the resulting solid was filtered and washed with 100 ml. of ether. After drying 3 hours at 30° C. to 35° C. there was obtained 10 g. (93% yield) of the title compound having consistent ir and nmr spectra.

EXAMPLE 7 p-Hydroxy-Ampicillin Methoxymethyl Ester Hydrochloride.

In 200 ml. of dichloromethane was slurried 20 g. of p-hydroxy-ampicillin, 20 g. of Linde type 4A molecular sieves and 6.6 ml. of triethylamine. After stirring about 1 hour at 0° C. to 5° C., this mixture was treated with 3.8 ml. of chloromethyl methyl ether, and stirred 2 hours at 0° C. to 5° C. The mixture was filtered and the clear filtrate washed with two 100 ml. portions of water at pH 7.0 to 7.5. The organic layer was then dried, treated with about 1 g. of decolorizing carbon and after filtration concentrated under reduced pressure at 30° C. to 40° C. to a foamy solid. IR and NMR spectra indicated about 10 to 15% of unchanged starting p-hydroxy-ampicillin and a slight excess of methoxymethyl groups suggesting some over-alkylation at the phenolic hydroxyl group or the amino group. A 6 g. sample of the product was dissolved in 60 ml. of dry acetone, cooled to 0° C. to 5° C. and 6 ml. of 13% HCl in 2-propanol added. The solution was rapidly added to 600 ml. of well stirred ether and after 5 minutes the resulting solid filtered, washed with ether and dried 3 hours 25° C. to 30° C. There was obtained 6 g. (91.5%) of p-hydroxy-ampicillin methoxymethyl ester hydrochloride as amorphous solid with IR and NMR spectra consistent with the structure and showing a small amount of acetone.

Table I, below, shows minimum inhibitory concentrations, in micrograms per ml., for the acetone adduct of the methoxymethyl ester of p-hydroxyampicillin (also called the methoxymethyl ester of p-hydroxyhetacillin; Cpd. B) against various organisms as compared to the minimum inhibitory concentration of ampicillin (Cpd. A).

TABLE I

| | Compounds | |
| Organism | A | B |
| --- | --- | --- |
| D. pneumoniae + 5% serum | .004 | .004 |
| Str. pyogenes + 5% serum | .004 | .004 |
| S. aureus Smith | .03 | .06 |
| S. aureus Smith + 50% serum | .06 | .06 |
| S. aureus BX1633 | 125 | 125 |
| S. aureus BX1633 | >125 | >125 |
| S. aureus | 125 | 125 |
| S. aureus | 125 | 125 |
| S. aureus | >125 | >125 |
| Sal. enteritidis | 0.13 | 0.13 |
| E. coli Juhl | 1 | 1 |
| E. coli | 32 | 32 |
| K. pneumoniae | 0.3 | 0.16 |
| K. pneumoniae | 125 | >125 |
| Pr. mirabilis | 0.16 | 0.16 |
| Pr. morganii | >125 | 32 |
| Ps. aeruginosa | >125 | >125 |
| Ser. marcescens | 32 | 32 |

Table II, below, shows some illustrative blood level data for the methoxymethyl ester of p-hydroxyhetacillin (1) after oral administration to mice as compared to ampicillin (2) and hetacillin (3).

TABLE II

Blood Levels after Oral Administration to Mice

| Compound | Dose (mg./kg.) | Blood Levels (µg/ml) .5 | 1 | 2 | 3.5 |
|---|---|---|---|---|---|
| | | Hours after Administration | | | |
| 1 | 50 | 4.8 | 3.5 | 1.7 | .7 |
| 2 | 50 | 3.3 | 2.1 | 0.9 | .5 |
| 3 | 50 | 2.0 | 1.8 | 1.1 | .5 |

In the treatment of bacterial infections in man, the compound of this invention is administered orally or parenterally, in accordance with conventional procedures for antibiotic administration, in an amount of from about 5 to 200 mg./kg./day and preferably about 5 to 20 mg./kg./day in divided dosage, e.g., three to four times a day. It is administered in dosage units containing, for example, 125 or 250 or 500 mg. of active ingredient with suitable physiologically acceptable carriers or excipients. The dosage units are in the form of liquid preparations such as solutions or suspensions or as solids in tablets or capsules.

EXAMPLE 8

Preparation of Crystalline Methoxymethyl 6-[D-(—)-2,2-Dimethyl-4-(4-hydroxyphenyl)-5-oxo-1-imidazolyl]-penicillanate.

To a stirred suspension of 24.3 g. (0.06 mole) of 6-[D-(—)-2,2-dimethyl-4-(hydroxyphenyl)-5-oxo-1-imidazolyl]penicillanic acid (p-hydroxyhetacillin) in 400 ml. of $CH_2Cl_2$ was added 6.72 ml. (0.054 mole) of triethylamine followed by 4 g. of Linde 4A molecular sieves. The mixture was stirred one hour and then filtered. The filtrate was stirred and cooled at —15° C. while 3.9 ml. (0.054 mole) of bromomethyl methyl ether was added dropwise over a 5 minute period. After stirring 30 minutes at —15° C., the solution was extracted with six 100 ml. portions of $H_2O$. The $CH_2Cl_2$ solution was then dried for ten minutes over $Na_2SO_2$ and filtered. The filtrate was evaporated under reduced pressure below 20° C. to give an oil which began to crystallize. The partially crystalline mass was dissolved in 50 ml. of $CH_2Cl_2$ and diluted to the cloud point with n-heptane. Scratching induced crystallization and after one hour at 22° C. the crystals were filtered off and discarded. The filtrate (mother liquor) was then diluted with 400 ml. of n-heptane and cooled in an ice bath. The oil which separated was then triturated with "Skellysolve B" which is a petroleum ether fraction of b.p. 60°–68° C. consisting essentially of n-hexane. This left a gummy material which was dissolved in a minimum amount of $CH_2Cl_2$. Almost immediately crystallization began - about two thirds of the $CH_2Cl_2$ was removed in vacuo and after standing two hours the crystals were collected by filtration and air dried to give 3.3 g. of product. A total of 3 g. of this material was recrystallized by dissolving it in 20 ml. of acetone, filtering and carefully diluting to the cloud point with n-heptane. The product, crystalline methoxymethyl 6-[D-(—)-2,2-dimethyl-4-(4-hydroxyphenyl)-5-oxo-1-imidazolyl]-penicillanate, was allowed to crystallize in large needles for two hours at 22° C., then two hours at 13° C., (cold room) and two hours at about 4° C. (ice bath). The crystals were then collected by filtration, washed with 3:2 n-heptane-acetone, then n-heptane and air dried. There was obtained 2.03 g., m.p. 112°–113° C. The ir and nmr were consistent with the desired structure indicating a purity of at least 90%.

Anal. Calcd. for $C_{21}H_{27}N_3O_6S$: C, 56.04; H, 6.00; N, 9.33. Found: C, 55.49; H, 5.96; N, 9.18; (uncorrected for 1.56% $H_2O$ as determined by the Karl Fischer method).

Table III

| Organism in Nutrient Broth | Sodium Ampicillin MIC (µg./ml.) | Amoxicillin Trihydrate MIC (µg./ml.) | Compound of Example 8 MIC (µg./ml.) |
|---|---|---|---|
| Str. pneumoniae* ($10^{-3}$)** | .016 | .016 | .008 |
| Str. pyogenes* ($10^{-3}$)** | .008 | .016 | .008 |
| S. aureus Smith ($10^{-4}$) | .06 | 0.13 | 0.13 |
| S. aureus+50% serum ($10^{-4}$) | 0.13 | 0.13 | 0.13 |
| S. aureus BX1633 ($10^{-3}$) | 32 | 16 | 16 |
| S. aureus BX1633 ($10^{-2}$) | >125 | >125 | >125 |
| S. aureus Meth.-Res. ($10^{-3}$) | 32 (37° C.) | 63 (37° C.) | 125 (37° C.) |
| | >125 (28° C.) | 32 (28° C.) | 63 (28° C.) |
| Sal. enteritidis ($10^{-4}$) | 0.13 | 0.25 | 1 |
| E. coli Juhl ($10^{-4}$) | 2 | 1 | 1 |
| E. coli ($10^{-4}$) | 16 | 16 | 32 |
| K. pneumoniae ($10^{-4}$) | 0.5 | 0.25 | 0.13 |
| K. pneumoniae ($10^{-4}$) | 125 | >125 | >125 |
| Pr. mirabilis ($10^{-4}$) | 0.25 | 0.25 | 0.25 |
| Pr. morganii ($10^{-4}$) | >125 | >125 | >125 |
| Ps. aeruginosa ($10^{-4}$) | >125 | >125 | >125 |
| Ser. marcescens ($10^{-4}$) | 32 | 32 | >125 |
| Ent. cloacae ($10^{-4}$) >125 | >125 | 125 | |
| Ent. cloacae ($10^{-4}$) | 32 | 63 | 125 |
| Ent. cloacae ($10^{-4}$) | 63 | 125 | 63 |

*45% AAB - 5% serum - 50% broth listed above,
**Dilution of overnight broth culture Additional information regarding the methoxymethyl ester of p-hydroxyhetacillin (referred to below as BL-P1780) has been obtained from the first measurements or oral absorption in man. The results are set forth briefly below and are also compared with the results of a previous, separate trial of the methoxymethyl ester of hetacillin which is referred to as BL-P1761 or sarpicillin and has been described in U.S. Pat. No. 3,996,236. Both esters hydrolyze eventually to their parent penicillins (i.e. amoxicillin and ampicillin) and therefore were administered in doses equimolar to the latter. Only the latter are biologically active per se. Also, both original ester and parent penicillin were measured.

Three formulations were each administered once orally to six (6) healthy adult male subjects in BL-P1780 Study 101 as follows:

FORMULATIONS

A. BL-P1780, 500 mg. (of amoxicillin-equivalent activity) as two 250 mg. buffered tablets.

B. BL-P1780, 500 mg. (an amoxicillin-equivalent activity) as two 250 mg. buffered tablets with 3.5 g. sodium bicarbonate being taken five minutes prior to the adminstration of BL-P1780.

C. Amoxicillin, 500 mg. as two 250 mg. capsules.

OBJECTIVES

The objectives of this study were three-fold:

1. To investigate the human safety and tolerance of single 500 mg. doses of BL-P1780.

2. To determine the effect of intragastric buffering with sodium bicarbonate on the absorption of BL-P1780.

3. To compare amoxicillin plasma and saliva concentrations and urinary excretion between BL-P1780 and amoxicillin.

RESULTS

Two of the six subjects were found to be consistently inordinately slow absorbers of both BL-P1780 and amoxicillin. This increased study variability made the statistical analyses of the data less reliable and would also result in an under-estimation of the true performance of BL-P1780. However, the intrastudy comparisons remain valid.

Intragastric buffering is not necessary to improve the bioavailability or tissue distribution of BL-P1780. There is some evidence that the best absorption and tissue distribution are achieved without intragastric buffering (i.e., with formulation A). When formulation A was compared to formula C (oral amoxicillin), it was found that BL-P1780 was more rapidly absorbed than amoxicillin and that true plasma amoxicillin levels after BL-P1780 and amoxicillin administration were statistically equivalent. The 0-24 hour urinary excretion of amoxicillin was significantly less after BL-P1780 administration (40.8%) than after amoxicillin administration (50.9%). Saliva amoxicillin levels after amoxicillin administration were detectable in only 3 of the 6 subjects and even then were low (maximum levels of 0.06 mcg./ml. and mean peak level of 0.03 mcg./ml.), delayed and erratic. After BL-P1780 administration, mean peak saliva amoxicillin levels were 10 to 20 times higher (0.6 mcg./ml.) and present from the first sampling time of 10 minutes until 3 hours.

The data for formulation A was compared to data from the previous BL-P1761 Study No. 122 for 500 mg. (as ampicillin-equivalent activity) of sarpicillin administered as two 250 mg. tablets without intragastric buffering. Plasma levels of the esters and of the antibiotics (true ampicillin and true amoxicillin) were very similar. Peak saliva ester levels and AUC (area under the curve) values are both 3 times greater after BL-P1780 administration than after sarpicillin administration. Peak saliva concentrations of true antibiotic are 2.5 times higher after BL-P1780 than after sarpicillin and saliva AUC values for true antibiotic are 1.8 times higher after BL-P1780 than after sarpicillin. Because of subject deficiencies, these are minimal estimates of the improved tissue distribution of amoxicillin from BL-P1780 over ampicillin from sarpicillin.

CONCLUSIONS

1. Based on the comparative saliva level data, amoxicillin from BL-P1780 has markedly improved tissue distribution over that of ampicillin, amoxicillin or ampicillin from sarpicillin.

2. Oral doses of BL-P1780 may yield plasma concentration of amoxicillin close to or equivalent to those found with equivalent oral doses of amoxicillin. Urine levels may be lower after BL-P1780 than after amoxicillin administration.

3. It is not necessary to neutralize the gastric contents to optimize BL-P1780 bioavailability. BL-P1780 may prove to be more available if the gastric contents are acidic (pH<3).

We claim:

1. The compound of the structure

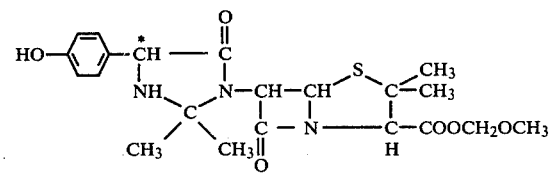

having the D-configuration at the carbon atom marked with an asterisk.

2. The hydrochloride of the compound of claim 1.

* * * * *